United States Patent [19]

Nunez

[11] Patent Number: 4,550,748
[45] Date of Patent: Nov. 5, 1985

[54] FLUID FLOW REGULATING UNIT FOR INTRAVASCULAR CATHETER SYSTEMS

[75] Inventor: Chris E. Nunez, Sandy, Utah

[73] Assignee: Warner-Lambert Company, Morris Plains, N.J.

[21] Appl. No.: 483,398

[22] Filed: Apr. 8, 1983

[51] Int. Cl.$^4$ ............................................. A61M 5/00
[52] U.S. Cl. ....................................... 137/605; 251/4; 251/117; 251/349; 604/250
[58] Field of Search ................... 137/605; 251/4, 117, 251/342, 349, 350; 604/246, 249, 250

[56] References Cited

U.S. PATENT DOCUMENTS 3,675,891  7/1972  Reynolds ........................ 251/117
4,192,303  3/1980  Young ............................ 604/250
4,245,636  1/1981  Sparks ........................... 604/249
4,267,835  5/1981  Barger ........................... 604/250

*Primary Examiner*—Robert G. Nilson
*Attorney, Agent, or Firm*—Louis S. Gillow

[57] ABSTRACT

A fluid flow regulating and control unit for intravascular catheter systems used in medical and surgical procedures with a slidably mounted closure member for the control fluid to the in-dwelling catheter. Force is exerted axially on an annular resilient member causing it to deform and bypass a relatively large flow of fluid through a fluid flow passage about the outer surface of a restrictor member therein; permitting the flow to pass with a predetermined minimum flow of fluid.

13 Claims, 14 Drawing Figures

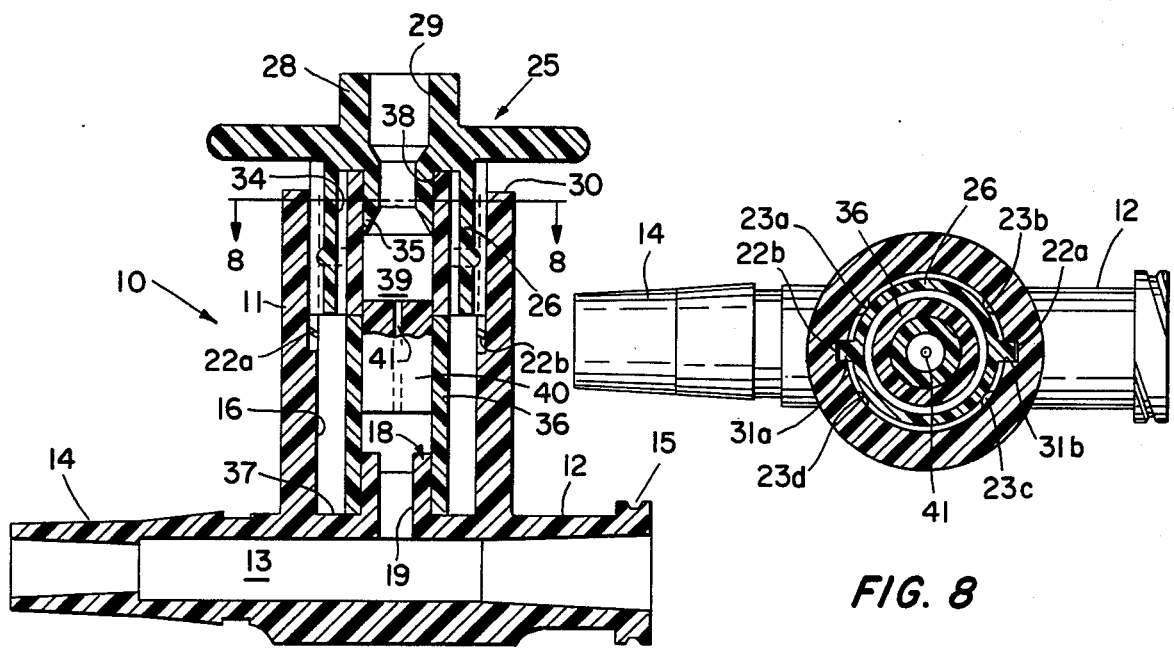
FIG. 4
FIG. 8
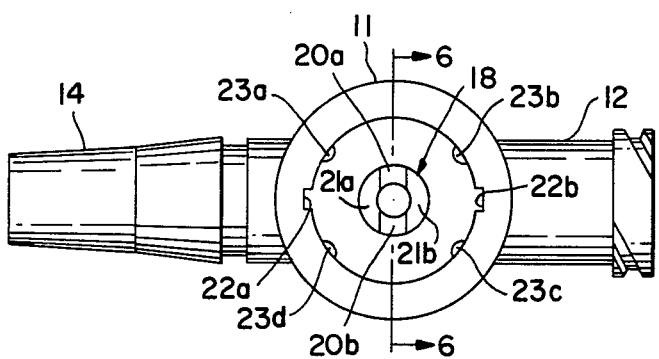
FIG. 5
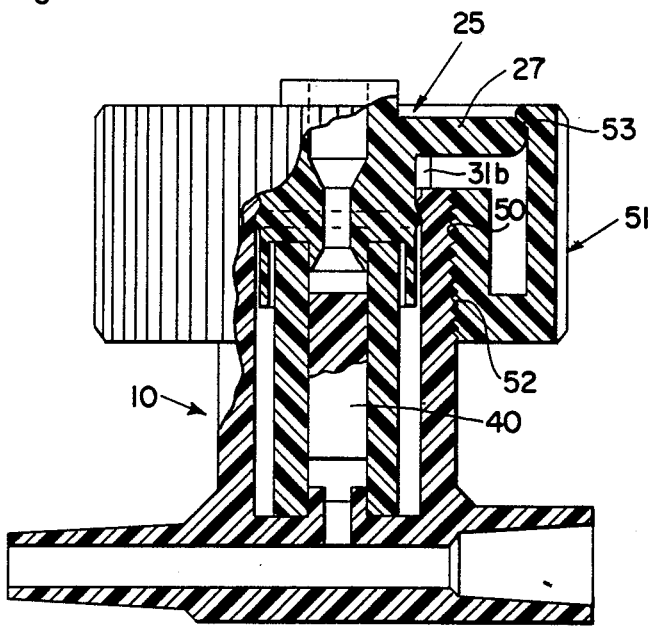
FIG. 9

FLUID FLOW REGULATING UNIT FOR INTRAVASCULAR CATHETER SYSTEMS

BACKGROUND OF THE INVENTION

1. Field:

This invention relates generally to intravascular catheter systems for introducing fluids, medications, and the like into a patient during medical and surgical procedures and for the clinical monitoring of blood and other parameters of the patient and more particularly to a fluid flow regulating and control unit adapted to regulate the flow of fluid in such system for reliable operation of the in-dwelling catheter in such intravascular catheter systems.

2. State of the Art:

It is well known that for the reliable operation of intravascular catheter systems it is necessary to continuously flush the in-dwelling catheter to maintain the end thereof, disposed in the patient, in an open condition.

Due to the importance of these systems in modern day medical and surgical treatment and procedures, various prior art apparatus has been developed. More recently, improved fluid flow control devices have been developed for use in such intravascular catheter systems as is shown in U.S. Pat. Nos. 3,675,891 and 4,192,303.

Each of U.S. Pat. Nos. 3,675,891 and 4,192,303 describes in detail the nature of intravascular catheter systems, the problems surrounding their operation, the existing prior art and the nature of the improvement set forth respectively in these patents. Accordingly the information disclosed in these patents is incorporated by reference. Broadly each of these patents describes a device for controlling the flow of fluid in the intravascular catheter system so as to provide two basic modes of flow, the first at a continuous relatively low rate and the second an intermittent manually controlled larger flow of fluid to rapidly flush the catheter in the intravascular catheter system from time to time to meet and overcome the problems of maintaining the in-dwelling catheter of these systems open for the reasons as set forth in these patents.

In U.S. Pat. No. 4,192,303 the control device disclosed is connected to the in-dwelling catheter in the intravascular catheter system there shown, to provide continuous flow of fluid to the catheter. Thus, the device includes an inlet and an outlet and a first fluid flow passage connecting the inlet to the outlet to pass fluid through the flow regulating and control device. At least a part of the first fluid flow passage comprises a section of flexible conduit and includes, a valve control means operatively associated with the section of flexible conduit so that when the flexible conduit is manually squeezed the valve control means therein is moved to an open position to permit a relatively large flow of fluid to pass through the first fluid flow passage for the required flushing mode for the in-dwelling catheter of the intravascular catheter system. The valve means will move to its normally closed position when the flexible conduit is released. A second passage is provided having a flow restriction means therein which is disposed relative to the valve control means so that when the valve control means is in the closed position, a predetermined continuous flow of the fluid being controlled is delivered to the outlet, thus bypassing the valve control means to provide the relatively low flow rate of the dual mode operation above described.

One of the problems of the flow regulating and control device disclosed in U.S. Pat. No. 4,192,303 is the fact that the section of flexible conduit is part of the exterior surface of the device and is manipulated by direct manual squeezing, thus presenting the possibility that the flexible section may be damaged inadvertently or otherwise which in the case of many patients who must undergo these required medical and surgical procedures may be subjected to life threatening conditions such as blood loss or failure to receive medication or needed fluids such as in the case of new born infants or the physically handicapped.

The present invention provides another improved flow regulating control unit which is adapted to meet and overcome the same problem overcome by the prior art U.S. Pat. Nos. 3,675,891 and 4,192,303 in which either the dual mode type operation may be utilized or wherein the flow of fluid to the catheter in the intravascular catheter system can be regulated from a predetermined minimum flow to the maximum flow capacity of the flow passage for the fluid being controlled by the flow regulating and control unit. The flow regulating and control unit in accordance with the present invention is characterized by the fact that the fluid flow passage between the inlet and the outlet includes a flexible conduit section which is protected within an operating chamber in the flow regulating and control unit. The fluid flow passage is provided with a continuously open connecting port so that the section of flexible conduit can coact with a restricting device for limiting the flow of fluid through the fluid flow passage. Thus, when axial forces are exerted against one end of the section of flexible conduit a predetermined flow of fluid can be bypassed about the flow restrictor and passed with the metered fluid through the continuously open connecting port to the outlet of the flow regulating and control unit.

SUMMARY OF THE INVENTION

Thus, the present invention covers an improved device for regulating the flow of flushing fluid in intravascular catheter systems, having a control housing defining an operating chamber open at one end, and having a transverse outlet manifold at the end opposite from said open end, a first guide support in said chamber having a continuously open connecting port communicating at one end with said transverse outlet manifold, a closure member having a sized flange thereon slidable mounted in the control housing for limited movement in the longitudinal line thereof, said closure member having a second guide support thereon extending into the operating chamber in alignment with the first guide support, and an outlet flow passage extending end to end through the closure member in the longitudinal line of said control housing, an annular section of resilient conduit connected at opposite ends to said first guide support and said second guide support and the inner surface of the annular resilient conduit forming a fluid flow passage connecting said inlet flow passage to the connecting port to permit fluid to flow from said inlet flow passage to said outlet manifold, sized restrictor means connected in generally sealing engagement with the inner surface of the annular resilient conduit to normally limit the flow through said fluid flow passage, and said closure member movable inwardly in the longitudinal line of said control member to exert an axial force on the resilient conduit to deform the same whereby a relatively large additional flow of flushing fluid bypasses the restrictor means until the closure member is released.

The fluid regulating and control unit as above described may also include threaded or helical means on the annular collar for operative engagement with the flange on said closure means for adjustably holding said closure member to regulate the quantity of fluid bypassing the restrictor means and permitting said increased quantity of fluid to bypass the restrictor means at this regulated setting until the threaded or helical means is readjusted.

Accordingly it is an object of the present invention to provide an improved flow regulating and control unit which is relatively simple in construction and therefore inexpensive.

It is another object of the present invention to provide an improved fluid flow regulating and control unit which is simple to operate and conceals and protects the section of resilient conduit which forms the fluid flow passage therein.

It is another object of the present invention to provide an improved fluid flow regulating and control unit for flushing fluid in an intravascular catheter system wherein the annular resilient conduit is operative to form the fluid flow passage therethrough and can be deformed by axial forces exerted thereon to adjustably bypass predetermined flows of fluids about a restrictor means for regulating the predetermined minimum quantities of fluid flowing through said fluid flow regulating and control unit.

Other objects and advantages of the present invention will become apparent from the following detailed description of the embodiments thereof taken together with the accompanying drawings.

DESCRIPTION OF THE FIGURES

FIG. 4 is a vertical section taken on line 4—4 of FIG. 2.

FIG. 5 is a top view of the control housing with the closure member, the resilient member, and the restrictor element removed.

FIG. 8 is a horizontal section taken on line 8—8 of FIG. 4.

FIG. 9 is a vertical section taken through another form of the fluid flow regulating and control device in accordance with the present invention.

DESCRIPTION OF ONE EMBODIMENT OF THE INVENTION

Figure 1:
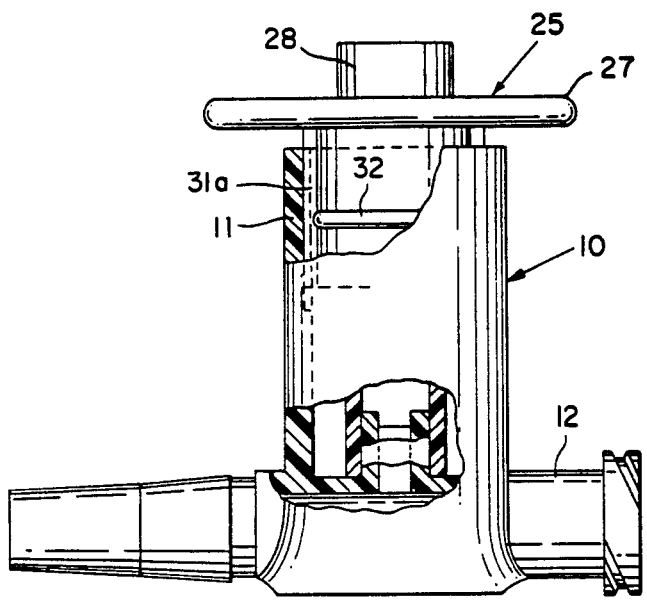
FIG. 1 is a side view of a fluid flow regulating and control unit in accordance with the present invention having portions thereof broken away in vertical sections.

Referring to the drawings, FIGS. 1 to 8 show one form of the fluid flow regulating and control unit generally designated 10 in accordance with the present invention having a generally cylindrical control housing 11 with an elongated transverse base section 12 at the lower end thereof through which an elongated outlet manifold 13 extends end to end therethrough.

A male luer connector 14 is provided on one end of the elongated transverse base section 12 and a luer lock threaded fitting 15 is formed on the opposite end so that the fluid flow regulating and control unit 10 can be connected to an arterial or venous catheter at one end and a monitoring gauge at the opposite end as will be understood by those skilled in the art, all of which is shown in FIGS. 1, 2, 3 and 4 of the drawings.

The control housing 10 can be cast, formed or molded from a plastic material which has suitable hardness to withstand the conditions of use and is chemically inert so that it will not react with the fluids flowing therethrough.

The cylindrical housing 11 defines an operating chamber 16 which is open as at 17 at the end thereof remote from the elongated transverse base section. In the end of the cylindrical housing adjacent to the transverse base section 12 a first guide support 18 is formed which projects into the operating chamber 16, as is shown in FIGS. 4, 5 and 6 of the drawings, and a connecting port 19 therein communicates at one end with the outlet manifold 13 to deliver the fluid being regulated and controlled thereto as will be more fully described below.

The connecting port at the end opposite from the outlet manifold communicates with side vents as at 20a and 20b formed in the first guide support member 18 so that fluid can pass freely into the connecting port 19 and thence to the outlet manifold 13. The upstanding side sections 21a and 21b of the first guide support 18 prevent the side vents 20a and 20b from being occluded during operation of the fluid flow regulating and control unit 10.

Figure 6:
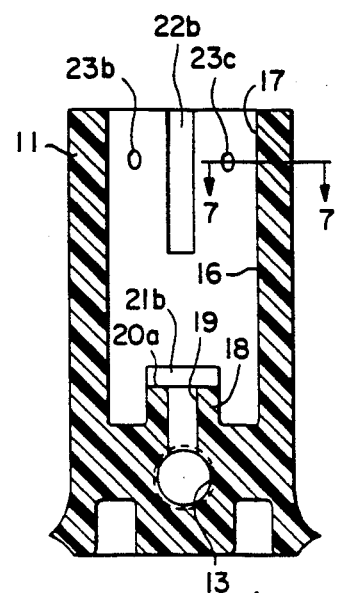
FIG. 6 is a vertical section of the control housing shown in FIG. 5 taken on line 6—6 thereof.

FIGS. 4, 5 and 6 further show that the cylindrical housing 11 is provided with spaced longitudinally extending grooves 22a and 22b. Inwardly from the open end 17 of the operating chamber 16 are a plurality of circumferentially spaced stop members as at 23a, 23b, 23c, and 23d. The longitudinally extending grooves 22a and 22b and the stop members 23a, 23b, 23c and 23d permit a closure member generally designated 25 to be slidably mounted on the cylindrical wall which defines the operating chamber 16 so that the closure member 25 will not separate from the control housing in assembled position as will now be described.

Figure 2:
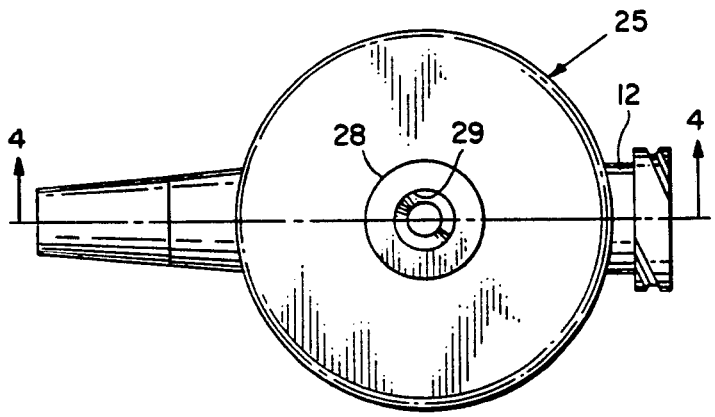
FIG. 2 is a top view of the fluid regulating and control unit shown in FIG. 1.
Figure 7:
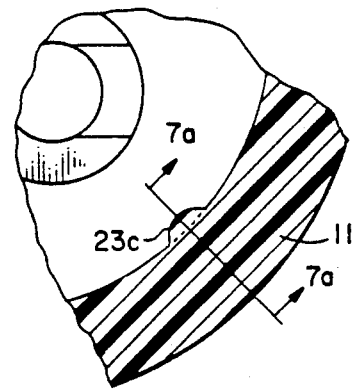
FIG. 7 is an enlarged view of one of the stop members on the inner wall of the control housing shown in FIG. 5 to prevent the closure member from being forced out of the open end of the control housing on expansion of the resilient conduit therein.
Figure 3:
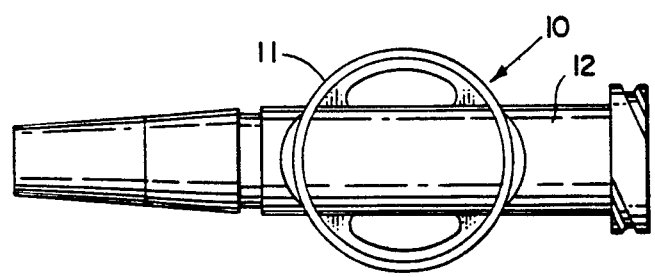
FIG. 3 is a bottom view of the fluid flow regulating and control unit shown in FIG. 1.
Figure 7A:
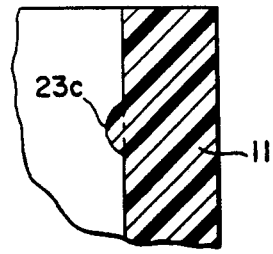
FIG. 7A is a fragmentary cross-section taken on line 7a—7a of FIG. 6.

Thus, referring to FIGS. 1, 2 and 4 of the drawing, the closure member 25 includes, a generally cylindrical center section 26, a flange 27 which is connected about the cylindrical center section, and a connector 28 which is disposed on the exterior surface of the closure member 25 so that when the closure member is in assembled position, the fluid flow regulating and control unit can be connected to the source of fluid to be controlled, an inlet flow passage as at 29 disposed to extend end to end through the connector 28 and the cylindrical section 26 to pass the fluid into the fluid passage 39.

The cylindrical center section 26 is sized for a sliding fit into the open end of the operating chamber 16. The annular flange 27 is sized so that it has a larger diameter than the open end of the control housing so that in assembled position on longitudinal inward sliding movement of the closure member 25, the flange 27 will come into contact with the end 30 of the cylindrical wall means forming the operating chamber in the control housing and thus will limit the inward movement of the closure member 25 for reasons that will be clear from the operation described below of the fluid regulating and control unit 10 in accordance with the present invention.

By further reference to FIGS. 1, 4 and 8 of the drawings, the closure member 25 is shown as having spaced key members 31a and 31b which are so positioned on the closure member 25 that when the closure member 25 is moved into assembled position they will engage and slide into the grooves 22a and 22b. The closure member 25 is also provided with a stop shoulder 32 which is circumferentially disposed transversely to the longitudinal line of the closure member 25 so that when the closure member is fitted into assembled position on upward movement thereof, the stop shoulder 32 will engage the stop members 23a, 23b, 23c and 23d as is shown in FIG. 8 of the drawings. The stop members and stop shoulder act to limit outward sliding movement of the closure member 24 when the member is in assembled position.

The cylindrical center section 26 of the closure member 25 is counterbored as at 34 to form a second guide support 35 disposed in assembled position substantially in the longitudinal axis of the control housing 11.

The first guide support 18 and the second guide support 35 are so aligned that a resilient annular member 36 can be swaged at each end onto the respective guide support 18 and 35 so that the inner periphery thereof defines a fluid flow passage 39 which enables fluid delivered to the inlet passage 29 to pass therethrough to the connecting port 19 and then to the outlet fluid manifold 13.

The resilient conduit member 36 is so sized that it fits into snug engagement at one end with the lower face 37 of the operating chamber 16 and at the opposite end with the end 38 of the counterbore 34 where the resilient conduit member 36 exerts a slight outward force on the closure member 25 causing the stop shoulder 32 to engage the stop members 23a, 23b, 23c and 23d and thus the closure member 25 is held firmly in its upper limit position in assembled position.

The closure member 25 is also cast, formed or molded from a suitable plastic material which is chemically inert and has good abrasion resistance for the operating conditions for the closure member 25.

The resilient annular member 36 is commercially available in conduits made from polysiloxanes which are chemically inert, capable of withstanding the hydraulic conditions of the system, and which provide the elastic properties necessary for the operation as hereinafter described for producing the additional desired fluid flow in the associated intravascular catheter system in which it is connected.

In order to provide the desired low rate mode of operation through the fluid flow passage 39, a restrictor member 40 is connected in the fluid flow passage 39, as is shown in FIG. 4 of the drawings.

The restrictor member 40 is a cylindrical element which has a substantially precise outer diameter so that when it is positioned in the fluid flow passage 39 as shown in FIG. 4, the outer diameter will form an interference fit with the inner periphery of the annular resilient conduit 36 so as to seal the flow of fluid from the inlet passage 29 to the connecting port 19 about the outer surface or outer periphery of the restrictor member 40. The restrictor member however is provided with the conventional orifice passage 41 extending end to end therethrough which then regulates and controls the predetermined minimum flow of fluid from the inlet passage 29 to the connector port and outlet fluid manifold 13 of the fluid flow regulating and control unit 10.

Since the connector port 19 is not valved, the predetermined minimum flow of fluid will be delivered continuously through the fluid flow regulating and control unit 10 at a low rate which will depend on the pressure and viscosity of the fluid entering through the inlet fluid passage 29.

Operation

When the closure member 25 is manually depressed it will act on the end portion of the annular resilient member 36 and cause the same to deform relative to the outer periphery of the restrictor element 40 so as to break the seal between the outer surface of the restrictor element 40 and the inner periphery of the annular resilient member 36. As a result depending upon the amount of axial force exerted on the annular resilient member 36, a more or less larger flow of fluid being controlled will be caused to bypass about the restrictor element 40. Thus, in addition to the predetermined minimum fluid flow passing through the restrictor 40, a relatively large flow of fluid will also pass to the connector port 19. This fluid, as will be understood by those skilled in the art, will be used for flushing the associated catheter of the intravascular catheter system and enable monitoring of the patient by any suitable gauge which may be connected to the respective connecting element 14 or 15 on the fluid flow regulating and control unit 10.

MODIFIED FORMS OF THE INVENTION

In FIG. 9 a modified form of the invention is shown in which a conventional orifice passage is not included and the flow regulating and control unit 10 is provided with threaded means as at 50 on the outer surface of and adjacent to the open end of the cylindrical control housing 11.

An annular collar 51 is internally threaded as to 52 so that it can be threadably connected to the control housing 11 as is further shown in FIG. 9.

The annular collar 51 is provided with an annular outer flange which forms an annular groove 53 on the outer face thereof which in assembled position forms a lost motion connection with the annular flange 27 on the closure member 25 so that the annular collar 51 is relatively rotatable with respect to the closure member 25 which is non-rotatable by reason of the key members 31a and 31b and at the same time can move the closure member 25 inward and outward by reason of the snug engagement of the outer periphery of the annular flange 27 with the annular groove 53 therein.

Thus, in assembled position the annular collar 51 can be threaded so as to rotate and axially move the closure member 25 a predetermined distance inwardly or outwardly thus controlling the degree of deformation of the annular resilient member 36 with respect to the restrictor element 40 thereby enabling a corresponding proportionate control of the fluid being controlled to flow about the external surface of the restrictor element 40 and to continuously maintain this flow until the annular collar 51 is reset to provide a different flow setting for the fluid flow regulating and control unit 10. Alternatively, in this modified form of the invention the threaded annular collar 51 could be replaced by a push or pull annular collar communicating with the closure member 25 so as to move the closure member 25 a predetermined distance inwardly or outwardly thus controlling the degree of deformation of the annular resilient conduit 36 with respect to the restrictor element 40 thereby enabling a corresponding proportionate control of this fluid being controlled.

In FIGS. 10–13 another modified form of the invention is shown in which a conventional orifice passage is not included and the flow regulating and control unit 10 is coaxial with the inlet 15 and the outlet 14 for fluid flow F.

The flow regulating and control unit 10 is provided with an annular collar 61 which is axially aligned and rotatably mounted on the control housing 11.

The annular collar 61 is provided with an annular ridge 55 on the distal end thereof for snap-fit engagement with an annular groove 56 on the surface of the control housing 11.

The annular collar 61 is provided with an annular outer flange 63 on the outer face of the proximal end thereof which in assembled position forms a helical connection with the inner annular flange 67 of the closure member 65 so that the annular collar 61 is relatively rotatable with respect to the closure member 65 and, at the same time, by action of the helix means as at 60 can move the inner annular flange 67 inward or outward by reason of the helical engagement as at 60 of the inner periphery of the annular outer flange 63 with the inner annular flange 67.

Figure 10:
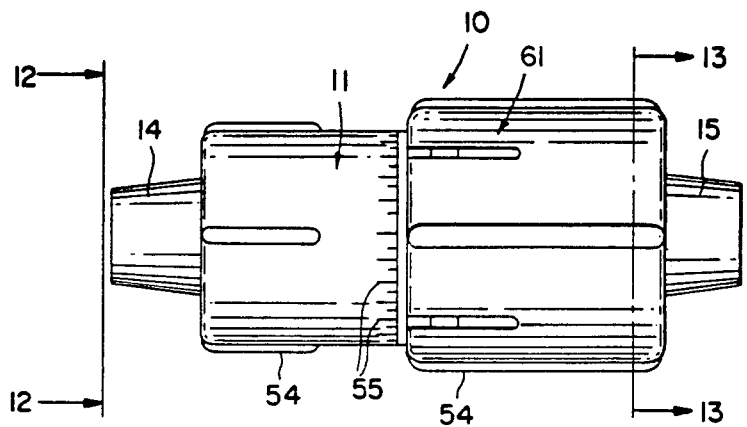
FIG. 10 is a top view of another form of the fluid flow regulating and control device in accordance with the present invention.
Figure 11:
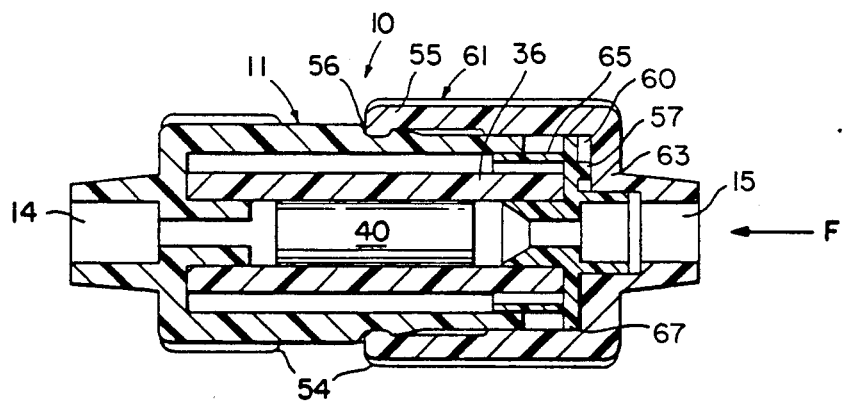
FIG. 11 is a vertical section of the device of FIG. 10 taken through the centerline thereof.
Figure 12:
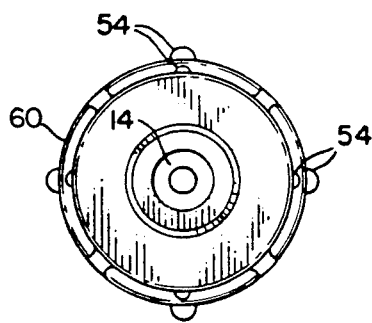
FIG. 12 is an end view from line 12—12 of FIG. 10.
Figure 13:
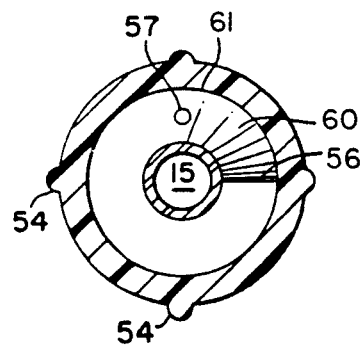
FIG. 13 is a cross-section of the annular collar member taken on line 13—13 of FIG. 10.

Thus, in the assembled position the annular collar 61 can be provided with a helix or partial helix 60 at the interior of the outer flange 63 so as to rotate and axially move the closure member 65 a predetermined distance inwardly or outwardly thereby controlling the degree of deformation of the annular resilient member 36 with respect to the restrictor element 40 and enabling a corresponding proportionate control of the fluid being controlled to flow about the external surface of the restrictor 40 and to continuously maintain this flow until the annular collar 61 is reset to provide a different setting in accordance with markings or settings 55 for the fluid flow regulating and control unit 10 as shown on FIG. 10. The fluid flow regulating and control unit 10 may be provided with gripping ridges 54 on either the cylindrical housing 11 or on the annular collar 61 as shown on FIGS. 10–13. The helix or partial helix 60 can be provided with a stop 56 on the inner periphery of the annular outer flange 63, as shown on FIG. 13, to engage with a limit tab 57 on the inner annular flange 67, as shown on FIG. 11, so as to limit the rotation of the annular collar 61 thereby limiting the axial motion of the closure member 65 which limits the amount of fluid flow through the flow regulating and control unit 10.

It will be understood that the invention is not to be limited to the specific construction or arrangement of parts shown but that they may be widely modified within the invention defined by the claims.

What is claimed is:

1. A fluid flow regulating and control unit for intravascular catheter systems used to infuse fluid, medication and the like in medical and surgical procedures comprising,
   a. a control housing having an operating chamber formed therein at one end and being open opposite thereto,
   b. a closure member slidably connected in the open end of the control housing for limited inward and outward movement relative to said operating chamber,
   c. said closure member having an inlet fluid passage for the fluid to be controlled,
   d. said control housing having an outlet manifold for the controlled fluid with at least one connector thereon for connection to the associated intravascular catheter system, and a continually open connecting port communicating at one end with the outlet manifold,
   e. an annular resilient member in the operating chamber connected at one end to the control housing about the connecting port and at the opposite end to the closure member, and the inner wall of the annular resilient member forming a fluid flow passage between the inlet fluid passage and the connecting port for the controlled fluid,
   f. a restrictor member mounted in interference fit with the inner wall of the annular resilient member, and
   g. said closure member and said annular resilient member operatively connected to each other to permit the closure member to exert axial forces on the annular resilient member to deform the same whereby the controlled fluid will flow around the restrictor member to the continuously open connecting port and into the associated outlet manifold for delivery to the intravascular system.

2. In a fluid flow regulating and control unit as claimed in claim 1 wherein the restrictor member has an orifice means therein to limit the flow of fluid through the fluid flow passage to a predetermined minimum.

3. In a fluid flow regulating and control unit as claimed in claim 1 wherein the annular resilient member is made of a polysiloxane material.

4. In a fluid flow regulating and control unit as claimed in claim 1 including,
   a. a first guide support means formed in the control housing about the connecting port,
   b. a second guide support means formed on said closure member about the inlet fluid passage and disposed in general alignment with the first guide support means,
   c. said annular resilient member connected to the first guide means and the second guide means so as to exert a slight axial force on the closure member to hold it in assembled position.

5. In a fluid flow regulating and control unit as claimed in claim 4 wherein the annular resilient member is made of a polysiloxane.

6. In a fluid flow regulating and control unit as claimed in claim 1 including means to prevent rotation of the closure member during sliding movement thereof.

7. In a fluid flow regulating and control unit as claimed in claim 1 including,
   a. stop means in the control housing adjacent to the open end of the operating chamber, b. a stop member on said closure member disposed in assembled position to engage said stop means to limit outward movement thereof, and c. means on the closure member to limit the inward movement thereof.

8. In a fluid flow regulating and control unit as claimed in claim 7 including means to prevent rotation of the closure member during sliding movement thereof.

9. In a fluid flow regulating and control unit as claimed in claim 1 including,
   a. threaded means formed on the control housing on the exterior surface and adjacent to the open end thereof,
   b. said closure member including a flange means and collar means having an internally threaded bore disposed to be threadably connected on the threaded section of the control housing, and the inner periphery of the collar means having a lost motion connection with the outer periphery of said flange means on the closure member whereby said collar means can be selectively and alternatively moved manually and threaded inwardly to regulate the flow of fluid bypassed about the restrictor means.

10. In a fluid flow regulating and control unit as claimed in claim 1 including,
    a. helical means and an open end formed together on the closure member on the exterior surface,
    b. said closure member including collar means having a bore disposed to be snap connected onto the outer surface of the control housing, and the inner periphery of the collar means having a helical connection with the helical means on the closure member whereby said closure member can be selectively and alternatively moved manually to regulate the flow of fluid bypassed about the restrictor means.

11. A fluid flow regulating and control unit for intravascular catheter systems used to infuse fluid, medication and the like in medical and surgical procedures comprising,
    a. control housing means having a cylindrical wall means defining an operating chamber open at one end,
    b. means connected to the control housing and opposite from the open end of the operating chamber having a transverse fluid flow passage extending end to end therethrough, and connecting means on each respective end for selectively and alternatively connecting catheters and monitoring gauges thereto,
    c. first guide support means formed in the control housing so as to project into the operating chamber,
    d. said first guide support having a continually open connecting passage in communication at one end with the transverse fluid flow passage,
    e. closure means having an annular flange slidably connected to said cylindrical wall means on the control housing to close the open end of said operating chamber and said annular flange disposed on inward movement of the closure member to engage the open end of the cylindrical means to limit inward movement thereof,
    f. said closure means having a second guide support disposed in assembled position to extend into the operating chamber in alignment with the first guide support,
    g. an annular resilient member connected at one end to the first guide support means and at the opposite end to the second guide support means and the inner periphery thereof defining a predetermined sized longitudinally extended fluid flow passage between the inlet passage and the connecting port,
    h. a cylindrical restrictive means having a sized outer diameter disposed in interference fit and general sealing engagement with the inner periphery of the resilient member and having an orifice therein to fix the predetermined minimum fluid flow passing from the inlet passage to the connecting port, and
    i. said closure member manually movable to exert an axial force on the end of said annular resilient member to deform the same whereby the seal between the restrictor means and the inner periphery of the annular resilient means will be sufficiently broken to bypass an additional and larger flow of fluid about the restrictor means to the connecting port to provide the desired flushing fluid for the flushing system.

12. In a fluid flow regulating and control unit as claimed in claim 11 including stop means formed on the cylindrical wall of the control housing inwardly of the open end, and a stop shoulder on the closure member operatively associated for engagement of the stop means to prevent the closure member from separating from the control housing.

13. In a fluid flow regulating and control unit as claimed in claim 11 including,
    a. spaced groove means extending into the cylindrical wall of the control housing from the open end thereof,
    b. key members formed on said closure member to mate and match with said groove means to prevent rotation of the closure means during operation of the regulating and control unit.

* * * * *